United States Patent [19]
Berry

[11] Patent Number: 5,668,123
[45] Date of Patent: Sep. 16, 1997

[54] METHOD OF MAINTAINING REMISSION FROM VENOUS ULCERS WITH SULPHASALAZINE AND ITS METABOLITE

[75] Inventor: Christopher Berry, Champigny sur Marne, France

[73] Assignee: Synthelabo, Le Plessis Robinson, France

[21] Appl. No.: 705,951

[22] Filed: Aug. 30, 1996

[30] Foreign Application Priority Data

Sep. 1, 1995 [FR] France ................... 95 10291

[51] Int. Cl.$^6$ .................................. A61K 31/615
[52] U.S. Cl. .................. 514/166; 514/925; 514/928
[58] Field of Search ..................... 514/166, 925, 514/928

[56] References Cited

U.S. PATENT DOCUMENTS

| | | | |
|---|---|---|---|
| Re. 33,239 | 6/1990 | Halskov | 206/213.1 |
| 4,970,301 | 11/1990 | Rolland et al. | 536/8 |
| 5,010,069 | 4/1991 | Bottom et al. | 514/166 |
| 5,384,134 | 1/1995 | Kross et al. | 424/661 |
| 5,519,014 | 5/1996 | Borody | 514/159 |
| 5,571,843 | 11/1996 | Cugnon De Sevricourt et al. | 514/590 |

FOREIGN PATENT DOCUMENTS

| | | |
|---|---|---|
| 0 352 826 | 1/1990 | European Pat. Off. . |
| WO86/03199 | 6/1986 | WIPO . |

OTHER PUBLICATIONS

The Merck Manual, 14th ed. p. 2033 1982.
Pooley, N. et al, "Up–Regulation of E–Selectin and Inter-–cellular Adhesion Molecule–1 Differs Between Crohn's Disease and Ulcerative Colitis", Dig.Dis.Sci., vol. 40, No. 1, Jan. 1995, pp. 219–225.
Wackers, F.J.T. et al, "Necrotizing Vasculitis and Ulcerative Colitis", Brit.Med.J., No. 5936, 1974, pp. 83–84.
O'Connor, C. et al, "Prevention of Recurrent Thrombosis In Antiphospholipid Syndrome (APS)", Arthritis & Rheumatism, vol. 38, No. 9SUP, 21, Oct. 26, 1995, p. S169.

*Primary Examiner*—Raymond Henley, III
*Attorney, Agent, or Firm*—Jacobson, Price, Holman & Stern, PLLC

[57] ABSTRACT

Method of treating venous insufficiency and venous ulcers by administering to a patient in need thereof an effective amount of sulphasalazine or 5-aminosalicylic acid.

3 Claims, No Drawings

METHOD OF MAINTAINING REMISSION FROM VENOUS ULCERS WITH SULPHASALAZINE AND ITS METABOLITE

The present invention concerns a method of treating venous insufficiency and venous ulcers (both ulcer healing and maintenance of remission) with sulphasalazine or its metabolite 5-amino salicylic acid (either as a monomer or dimer).

Sulphasalazine and its active metabolite 5-aminosalicylic acid (5-ASA) have been used almost exclusively for the past 50 years in the treatment and the maintenance of remission of ulcerative colitis and Crohn's disease. The etiology of these pathologies has still not been elucidated but certain contributory factors have been recognised. For example, ulcerative colitis is characterised by monocyte activation resulting in an increase in the release of Tumor necrosis factor $\alpha$ (TNF$\alpha$), increased leukotriene levels, polymorphonuclear cell (PMNs) activation, free radical release and post-capillary constriction (Casellas et al., *Clin. Sci.*, 87, 453–458, 1994; Uchida et al., *Clin. Biochem.* 27, 259–264, 1994, "Inflammatory bowel disease" J. B. Kirsner, Ed., Lea & Febiger, Philadelphia, 1988). Moreover, local thrombosis and tissue infarction have been proposed as contributory factors to Crohn's disease (Wakefield et al., *Lancet*, ii, 1057–1062, 1989).

The mechanism of action of sulphasalazine and 5-ASA in the treatment of ulcerative colitis is unknown. Sulphasalazine and 5-ASA inhibit the synthesis of peptido-leukotrienes (Peskar et al., *Agents and Actions*, 18, 381–383, 1986; Berry et al., *Br. J. Pharmacol.*, 93, 141P, 1988). Sulphasalazine inhibits 15-hydroxy prostaglandin dehydrogenase (Berry et al., *Biochem. Pharmacol.*, 32, 2863–2871, 1983). Both compounds are free radical scavengers (Ronne et al., *Gastroenterology*, 98, 1162–1169, 1990). They inhibit neutrophil activation in vitro (Molin & Stendhal, *Acta. Med. Scand.*, 206, 451–457, 1979), cytokine release by monocytes (Lamming et al. *Gastroenterology*, 96, A525, 1989), and recently sulphasalazine has been shown to lead to a decrease in E-selectin and intercellular adhesion molecule-1 (ICAM-1) expression in vitro using cultured human umbilical vein endothelial cells (Pooley et al. *Dig. Dis. Sci.*, 40, 219–225, 1995).

The chronic venous hypertension associated with venous insufficiency has repercussions on skin microcirculatory function. White blood cells, notably monocytes and PMNs cross the capillary network more slowly and become activated (Butler et Coleridge Smith, *J. Dermatol. Surg. Oncol.*, 20, 474–480, 1994). Once activated, these cells adhere to the walls of the post capillary veinules accompanied by the liberation of inflammatory mediators, which can contribute to tissue destruction associated with ulcer formation. Venous insufficiency is often a sequel of venous thrombosis. Moreover, clinical trials with pentoxyfylline, which is capable of inhibiting neutrophil activation have shown promising results in accelerating the healing rate in patients with venous ulcers.

The applicant showed for the first time the effect of sulphasalazine on white cell rolling and adhesion in vivo in rat mesenteric post-capillary veinules. The results obtained in this test show that topical application of sulphasalazine to the mesenteric vasculature in the rat leads to a dose-dependent decrease in white cell activation induced by f-met-leu-phe. This inhibition is significant as from 1 mM sulphasalazine.

Thus sulphasalazine and its active metabolite 5-ASA can be used for the treatment of venous insufficiency and venous ulcers, both for curative treatment and as maintenance therapy for the maintenance of remission.

The compounds can be given in all pharmaceutical forms adapted for oral or topical administration with appropriate excipients adapted to enable the daily administration of 0.1 to 4 g of active substance.

I claim:

1. Method of treatment in order to maintain remission from venous ulcers which comprises administering to a patient in need thereof an effective amount of sulphasalazine or 5-aminosalicylic acid.

2. Method of treatment according to claim 1 wherein treatment is administered by the oral route.

3. Method of treatment according to claim 1 wherein treatment is administered by topical route.

* * * * *